(12) United States Patent
Dunger

(10) Patent No.: US 6,696,414 B2
(45) Date of Patent: Feb. 24, 2004

(54) USE OF GROWTH HORMONE IN LOW DOSE

(75) Inventor: David B. Dunger, Cambridge (GB)

(73) Assignee: Pharmacia AB, Stockholm (SE)

( * ) Notice: Subject to any disclaimer, the term of this patent is extended or adjusted under 35 U.S.C. 154(b) by 65 days.

(21) Appl. No.: 09/804,775

(22) Filed: Mar. 13, 2001

(65) Prior Publication Data

US 2001/0051601 A1 Dec. 13, 2001

(30) Foreign Application Priority Data

Mar. 13, 2000 (SE) ................................................ 0000837

(51) Int. Cl.⁷ .......................... A61K 38/00; A61K 38/27
(52) U.S. Cl. .......................... 514/12; 514/866; 514/909; 930/120
(58) Field of Search .......................... 514/12, 909, 866; 930/120

(56) References Cited

U.S. PATENT DOCUMENTS

| | | | |
|---|---|---|---|
| 4,670,393 A | | 6/1987 | Seeburg |
| 5,079,345 A | * | 1/1992 | Becker et al. ............... 530/399 |
| 5,597,709 A | * | 1/1997 | Rossen et al. ............. 435/69.4 |

FOREIGN PATENT DOCUMENTS

| | | |
|---|---|---|
| EP | 0534568 | 3/1993 |
| WO | WO 9004788 | 5/1990 |
| WO | WO 9005185 | 5/1990 |
| WO | WO 9409813 | 5/1994 |
| WO | WO 9709060 | 3/1997 |
| WO | WO 9738709 | 10/1997 |
| WO | WO 9901151 | 1/1999 |

* cited by examiner

*Primary Examiner*—Yvonne Eyler
*Assistant Examiner*—Fozia Hamud
(74) *Attorney, Agent, or Firm*—Dinsmore & Shohl LLP

(57) ABSTRACT

The invention relates to treatment of patients in need of increasing insulin sensitivity by administration of growth hormone or analogues thereof, preferably human growth hormone, in a low dose and the use of growth hormone or analogues thereof, preferably human growth hormone, for the manufacturing of a medicament useful for increasing insulin sensitivity in low dose therapy.

Figure 1:
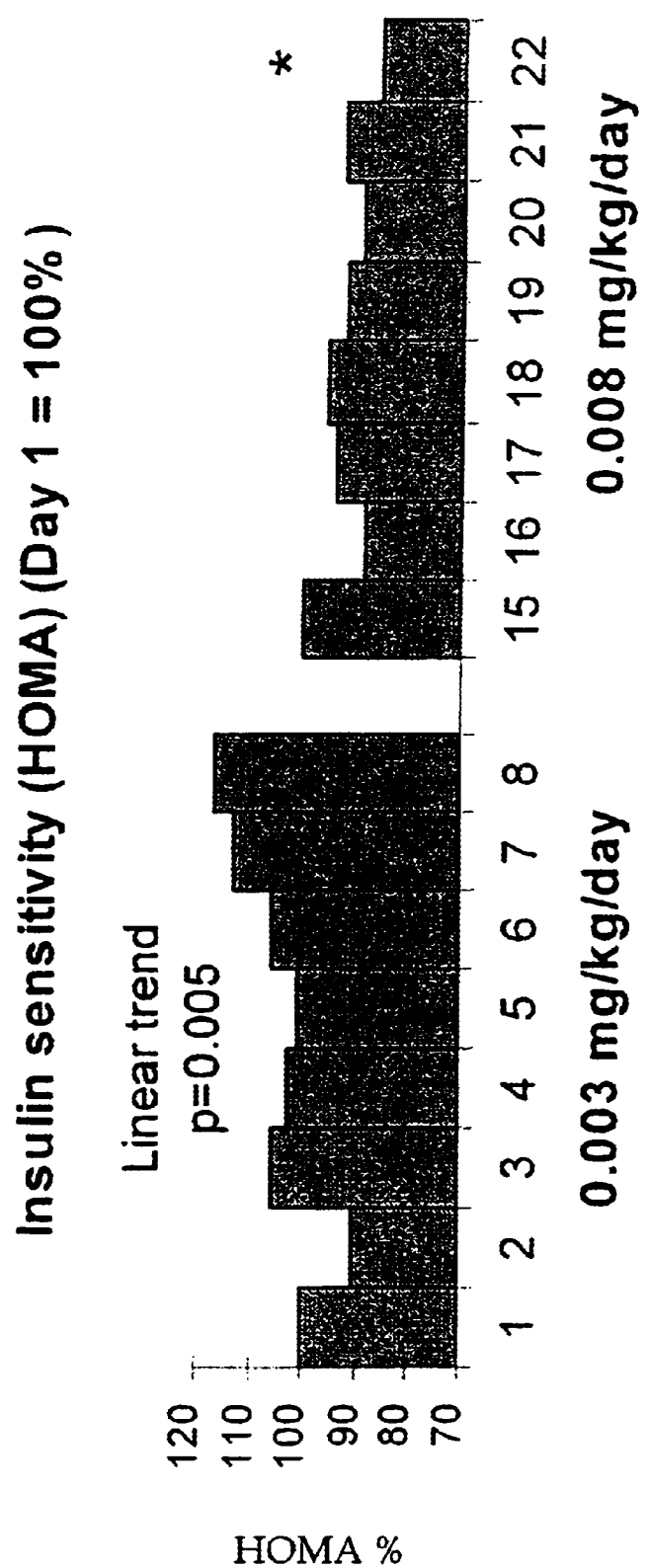

The patient is preferably a normal subject, i.e. not growth hormone deficient patient and/or a non-obese patients.

By low dose therapy is preferably meant less than 0.008 mg/kg/day, preferably 0.007 mg/kg/day or less, more preferably 0.005 mg/kg/day or less and most preferably 0.003 mg/kg/day or less.

The therapy is preferably performed during short term treatment, preferably less than one month.

12 Claims, 6 Drawing Sheets

USE OF GROWTH HORMONE IN LOW DOSE

The present invention relates to treatment of patients in need of increasing insulin sensitivity by administration of growth hormone or analogues thereof, preferably human growth hormone, in a low dose and the use of growth hormone or analogues thereof, preferably human growth hormone, for the manufacturing of a medicament useful for increasing insulin sensitivity in low dose therapy.

BACKGROUND

Human Growth Hormone, hGH, is a protein consisting of a single chain of 191 amino acids. The molecule is cross-linked by two disulfide bridges and the monomeric form has a molecular weight 22 kDa. hGH preparations have been prepared from human pituitaries, but nowadays the products on the market are produced by recombinant methods, rhGH. Two types of therapeutically useful recombinant hGH preparations are present on the market: the recombinant hGH, e.g. Genotropin®, Pharmacia AB, and an analogue of the recombinant hGH with an additional methionine residue at the N-terminal end, e.g. Somatonorm®. hGH is used to stimulate linear growth in patients with hypopituitary dwarfism or Turner's syndrome but other indications have also been suggested.

Growth hormone therapy is used in children to promote growth and in adults to improve muscle strength, reduce fat mass and improve metabolic profiles, which could predispose to cardiovascular disease. In contrast to the growth promoting effects of growth hormone, the metabolic effects have been less often studied, yet they may be very important to the risk-benefit assessment of GH therapy in adults.

GH therapy is known to counter insulin actions and is contra-indicated for individuals with diabetes mellitus.

At present GH therapy in adults is monitored using serum IGF-I levels, but it is possible that it is the metabolic effects which are more relevant to improvements in symptomatology and disease risk profiles and there is a need to develop ways of formally assessing these responses.

PRIOR ART

Growth hormone replacement supplementation to hypophysectomized rats has been shown to improve glucose uptake in the diaphragm muscle, see Diabetes, 1962, Vol. 11 (3), pp. 171–178. By contrast, pharmacological treatment with GH, resulting in supra-physiological circulating levels of the hormone, is known to produce a decrease in total body glucose uptake and disposal as well as a blunted metabolic response to insulin (i.e. insulin resistance) in skeletal muscle, see Hettiarachchi M et al., Diabetes 45(4):415–21, 1996. However, in tissues which are metabolically markedly different from the muscle, like adipose tissue, GH could induce glucose up-take, as reported in Endocrinology, 1996, Vol. 137(11), pp. 4650–5 M Ridderstråle et al.

Koller J et al, Acta Chirurgiae Plasticae, (1998) 40/3 (76–78) disclose the growth hormone effect in burn treatment. rhGH was administered at daily doses of 0.52 i.u./kg starting on day 19 post-burn for 15 consecutive days. It is stated that the treatment was well tolerated except for mild insulin resistance.

Initial studies of GH replacement in hypopituitary adults used high daily GH doses (0.07 IU/kg BW; ~3 IU/m2; ~5 IU/day) based on experience in children (Salomon F et al. *NEJM* 1989; 321: 1797–1803.). However, these studies were associated with an increased incidence of side-effects (mainly salt and water retention), which usually resolved on reduction in dosage. In sequential studies using half this dose (0.035 IU/kg BW; ~1.5 IU/m2; ~2.5 IU/day), the incidence of side-effects decreased significantly (Mardh G, et al. *Endocrinol Metab* 1995; 2: 11–16). This is also in agreement with using lower doses in adults than in children as physiological GH production decreases with ageing (Iranmanesh A et al. *J Clin Endocrinol Metab* 1991; 73: 1081–1088.). Rosenfalck et al recently demonstrated the beneficial effects of a relatively low dose of GH replacement therapy (mean dose of 1.6 IU/day) in GH-deficient adults on body composition with an increase in lean body mass and a reduction in body fat. In spite of these favourable changes, a deterioration in insulin sensitivity was observed with a quarter of the patients developing impaired glucose tolerance (Rosenfalck A M, et al *J Clin Endocrinol Metab* 2000; 11: 4173–4181). In 1998, the Growth Hormone Research Society recommended that GH replacement was commenced at a low dose (0.45–0.9 IU/day), and increased gradually on the basis of biochemical and clinical response at intervals greater than 1 month (Carroll P V et al. *J Clin Endocrinol Metab* 1998; 83; 382–395.). Murray et al recently demonstrated that baseline serum IGF-I SD is the only determinant required for optimal GH replacement therapy in GH-deficient adults (Murray R D et al. *Clinical Endocrinology* 2000; 52: 537–542.).

WO9409813 discloses a method for treating obesity by the administration of GH and IGF-I. The dose of GH should be at least 0.01 mg/kg/day.

WO9532991 discloses the combined administration of human growth hormone and dehydroepiandrosterone to regenerate human thymus to allow intra-thymic transplantation to eliminate organ and tissue rejection. The hyperinsulinaemia side effects of growth hormone are thereby eliminated e.g. hyperinsulinaemia in children, i.e. no elevation in blood levels of insulin are observed.

In WO97/38709 obese subjects have been treated with GH to find the potential for growth hormone to reduce central obesity.

The subjects treated had a body mass index between 25 and 35 kg/m$^2$, an IGF-I less that 160 µg/L (low normal) and a waist hip ratio of more that 0.95. The study was performed for 9 months with the administration of rhGH. The daily rhGH dose was 0.0095 mg/kg (0.20 IU/kg body weight/ week), administrated subcutaneously before bedtime.

Lipoprotein lipase (LPL) activity and Glucose disposal rate (GDR) were observed in this study.

The patients in WO97/38709 are obese and rhGH was given for 9 months. No conclusion can be drawn from this study for treatment of normal individuals with low dose GH treatment.

WO9901151 relates to a therapy involving administration of human growth hormone for improving cellular function in the heart challenged by insulin resistance and thereby treating or protecting the heart from complications derivable from this condition. Only complications resulting from insulin resistance in the heart are mentioned.

In none of these references has a low dose of growth hormone been given to normal subjects and no conclusion regarding insulin sensitivity can be drawn from the earlier reported findings.

FIGURES

The Figures illustrates the invention.

FIG. 1 % Insulin sensitivity (HOMA, Day 1=100%) (0.003 and 0.008 mg/kg/day)

Figure 2:
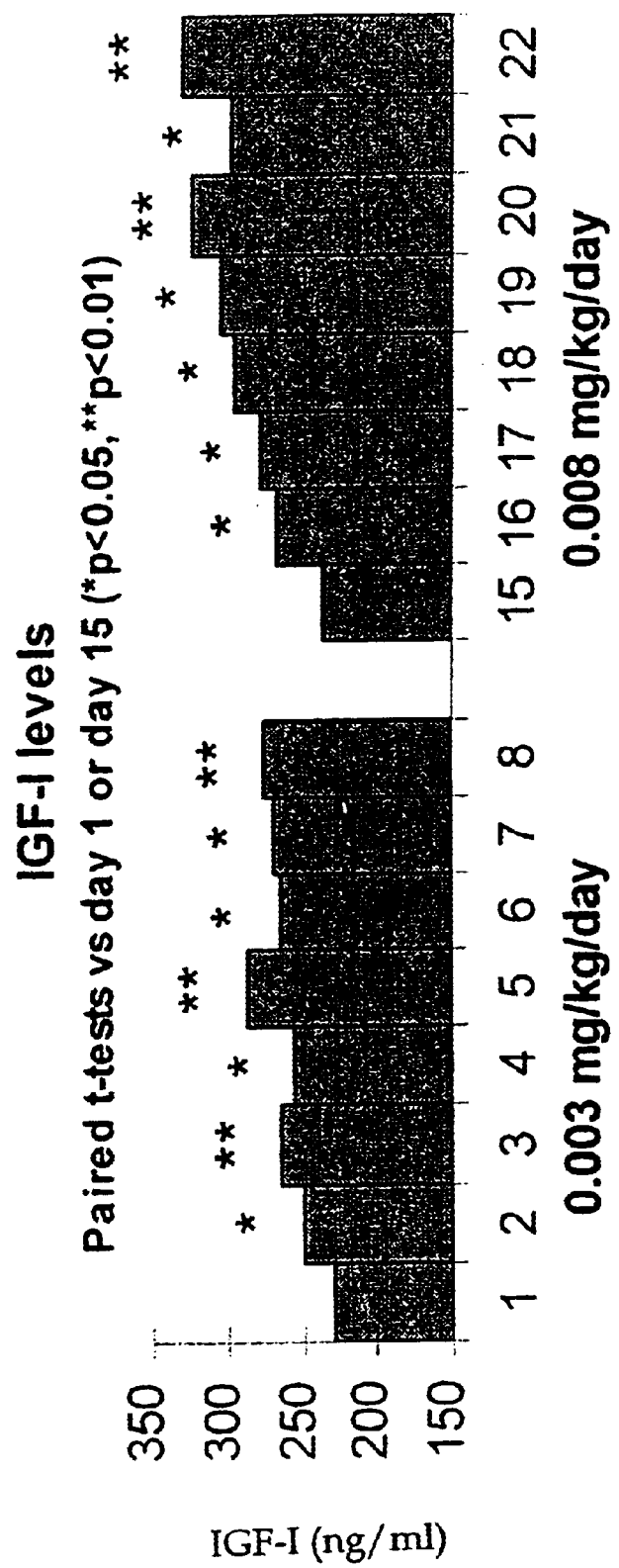

FIG. 2 mean IGF-I levels on GH therapy I (0.003 and 0.008 mg/kg/day)

Figure 3:
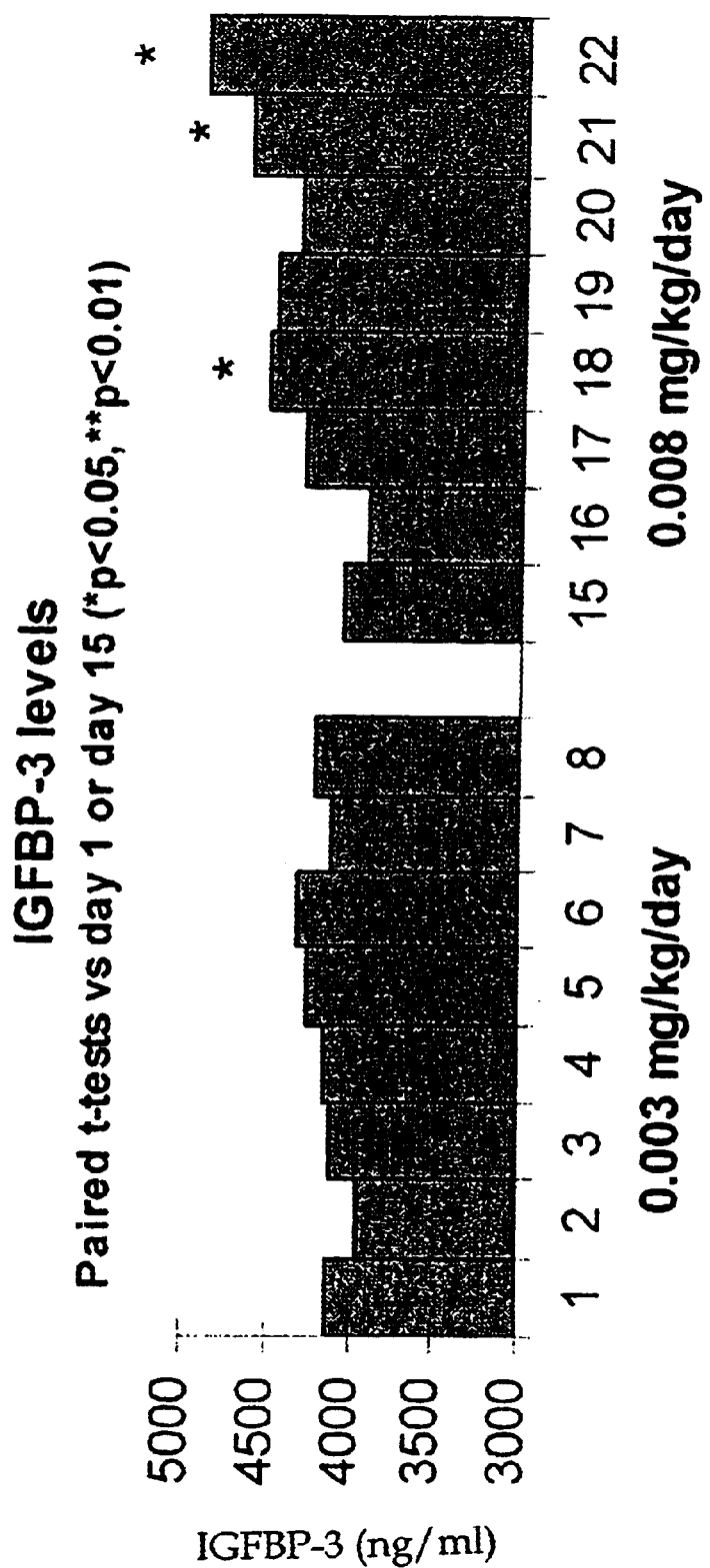

FIG. 3 mean IGFBP-3 levels on GH therapy (0.003 and 0.008 mg/kg/day)

Figure 4:
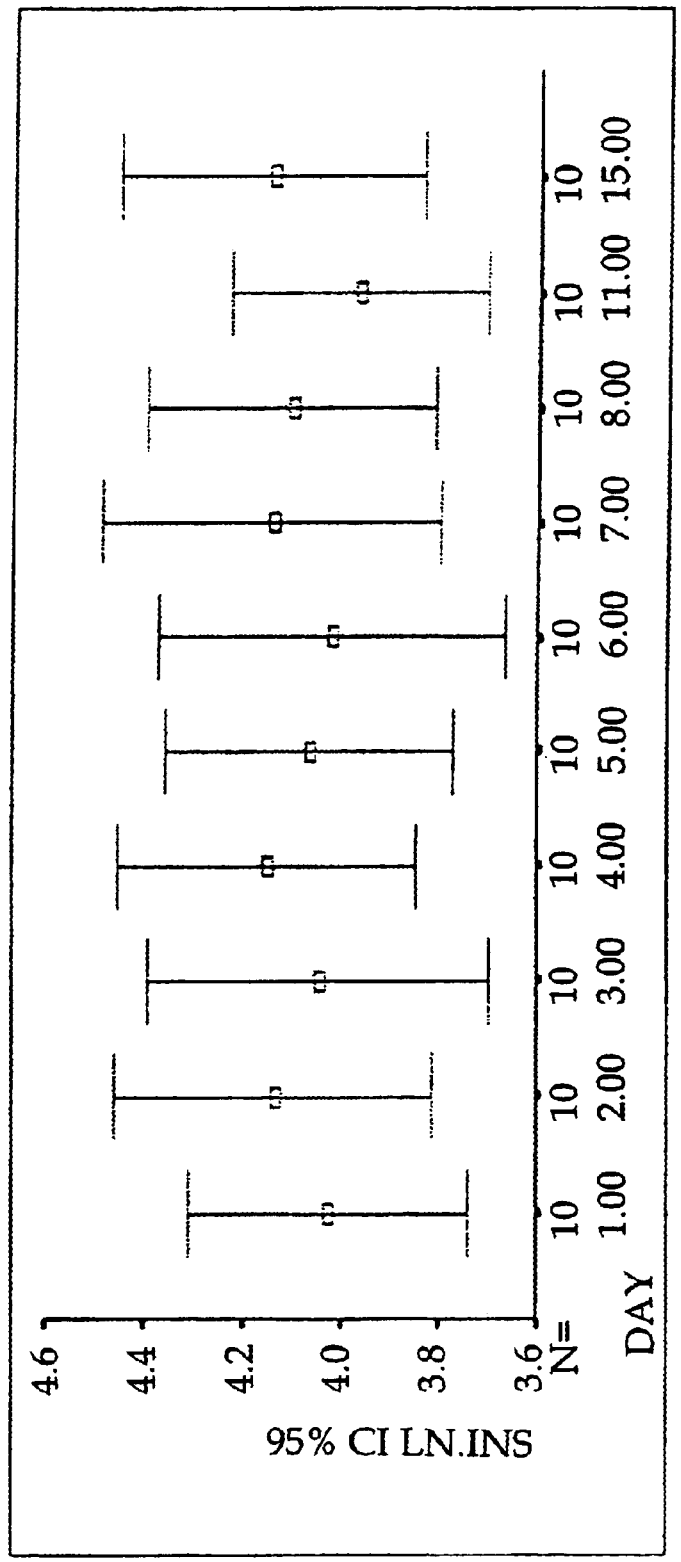

FIG. 4. Insulin levels on GH therapy (0.0016 mg/kg/day)
FIG. 5 Glucose levels on GH therapy (0.0016 mg/kg/day)
FIG. 6 HOMA beta cell function on GH therapy (0.0016 mg/kg/day)

THE INVENTION

We have now found that low dose growth hormone (GH) therapy can induce sustained improvements in insulin sensitivity in normal subjects. This is in contrast to current dogma which indicates that that GH only has transient insulin-like effects and generally leads to insulin resistance. One would predict from prior art, that giving GH to normal subjects would lead to peripheral insulin resistance and compensatory hyperinsulinaemia, and certainly this was not what was observed at the lower dose here administrated. Our observation of improved insulin sensitivity in these normal subjects given the lower dose of GH is a novel finding and quite unpredictable.

The insulin resistance observed in adult GH deficient subjects is paradoxical, because growth hormone deficiency in young children leads to increased insulin sensitivity. In the GH deficient children studied, younger children tend to be insulin sensitive whereas the older ones become insulin resistant. Thus when we treat adult GH deficient patients with GH, improvements in insulin sensitivity could result just from redistribution of fat or from increased IGF-I levels.

Our finding that the effects of low dose GH in normal subjects, (non-obese, non-GH deficient), in particular, subjects who may be insulin resistant and genetically predisposed to syndrome X is of great importance. The ability to improve insulin sensitivity in these subjects using low doses of GH is an unexpected finding.

This invention relates to the findings that ultra-low dose GH may paradoxically improve insulin sensitivity in contrast to higher doses which cause a decline in insulin sensitivity and these differences may relate to different bio-availability and inhibition of IGF-I by binding proteins in these normal subjects. These data indicate a novel and unique indication for low dose GH treatment in subjects with impaired glucose tolerance or insulin resistance who are subsequently prone to develop type 2 diabetes and syndrome X as such treatment might reduce insulin resistance and susceptibility to disease in these subjects.

Our invention relates to a method for treatment of patients in need of increasing insulin sensitivity which method comprises the administration of growth hormone or analogues thereof in a low dose.
The growth hormone is preferably human growth hormone and more preferably recombinant growth hormone.
The patient is preferably a normal subject, i.e. not growth hormone deficient patient and/or a non-obese patients.
By low dose therapy is preferably meant less than 0.008 mg/kg/day, preferably 0.007 mg/kg/day or less, more preferably 0.005 mg/kg/day or less and most preferably 0.003 mg/kg/day or less.
The therapy is preferably performed during short term treatment, preferably less than one month.

The invention also relates to the use of growth hormone, preferably human growth hormone or analogues thereof for the manufacturing of a medicament useful for increasing insulin sensitivity, preferably in non-obese patients, more preferably in non growth hormone deficient patients when given as low dose therapy, preferably less than 0.008 mg/kg/day and more preferably 0.007 mg/kg/day or less, preferably during less than one month.

The homeostasis model assessment (HOMA) is a model used to estimate insulin sensitivity (and also beta-cell function) from fasting plasma glucose levels and insulin concentrations. (See Matthews D R et al. 1985, Homeostasis model assessment: insulin resistance and beta-cell function from fasting plasma glucose and insulin concentrations in man. Diabetologia. 28:412–419).

EXAMPLE 1

Twelve GH normal adults, age between the ages of 16 and 40 years and normal body mass index were used for the study.

A dose of 0.003 mg/kg/day of GH was given for a period of 7 days, followed by a wash out period for 1 week and thereafter a GH treatment of 0.008 mg/kg/day during 7 days. The results can be seen on FIGS. 1 to 3.

FIG. 1 shows that HOMA (Day 1=100%) was higher after the first day when 0.003 mg/kg/day was given in comparison to 0.008 mg/kg/day. This clearly shows the increase in insulin sensitivity effect when the low dose was given in comparison to the higher dose of 0.008 mg/kg/day.

FIG. 2 shows mean IGF-I levels, which increase significantly from baseline on both 0.003 mg/kg/day and 0.008 mg/kg/day doses). In contrast IGFBP-3 levels remained unchanged on the 0.003 mg/kg/day dose, and only showed an increase on the higher 0.008 mg/kg/day dose.

This study shows that in GH normal adults, low dose GH therapy (0.003 mg/kg/day or at least less than 0.008 mg/kg/day) results in improvement in insulin sensitivity. This is accompanied by a significant increase in IGF-I levels but not in the IGF-I major binding protein IGFBP-3, suggesting that the changes in insulin sensitivity may relate to improvement in IGF-I bioavailability.

EXAMPLE 2

A dose of 0.0016 mg/kg/d (0.005 IU kg/d) of GH was given for 15 days to normal volunteers.

Figure 5:
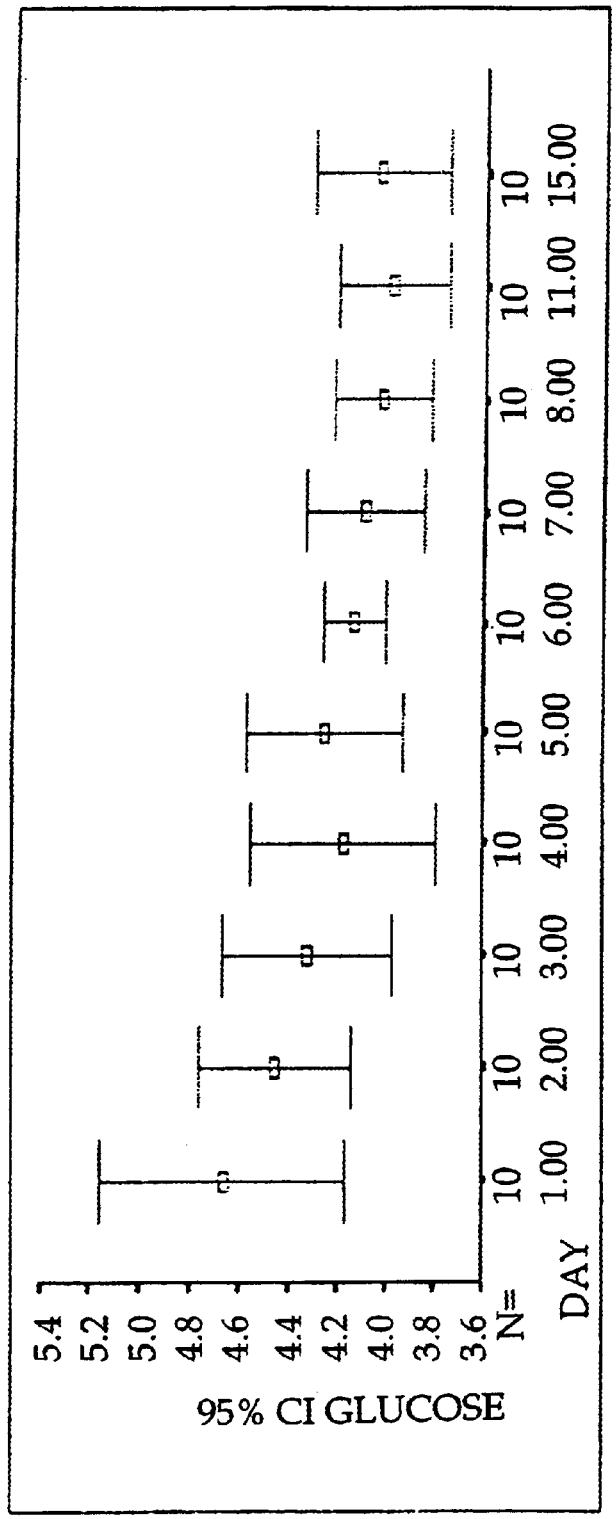
Figure 6:
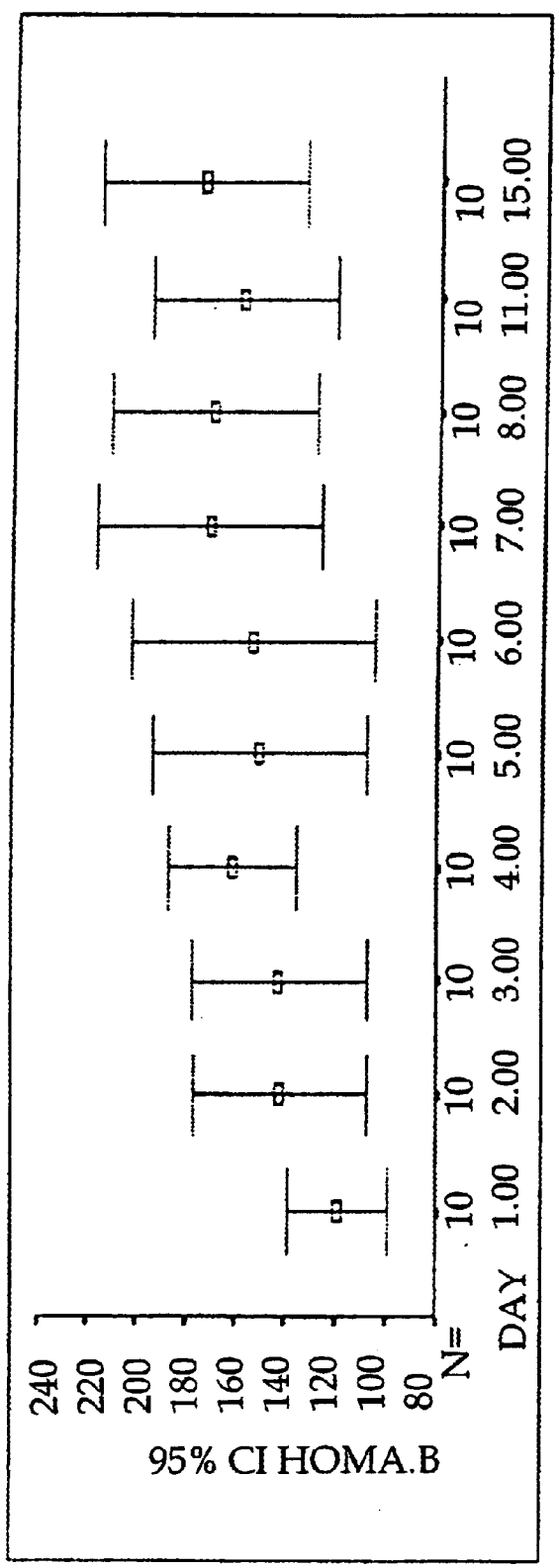

Glucose levels fell consistently over the treatment period (p=0.00017), whereas insulin levels were unchanged. FIG. 4 shows the Insulin levels, FIG. 5 shows the Glucose levels and FIG. 6 shows HOMA beta cell function over the period.

The glucose levels fell significantly over the 15 day period, which is an unexpected finding of high therapeutic value.

This even lower dose GH therapy (0.0016 mg/kg/day) again resulted in an improvement in glucose-insulin homeostasis. HOMA interpreted this as an improvement in beta-cell a function (p=0.00017), which is reminiscent of reports of GH on beta-cell function and induction of hypoglycaemia), rather than in insulin sensitivity. However, we suspect that this could be an anomaly of HOMA which was not designed to detect improvements in insulin sensitivity beyond the normal range.

What is claimed is:

1. Method for increasing insulin sensitivity in a non-obese, non-growth hormone deficient patient, which method comprises the administration of growth hormone or a growth hormone analogue having an additional methionine residue at the N-terminal end to the patient in a low dose.

2. The method according to claim 1, wherein the dose is less than 0.008 mg/kg/day.

3. The method according to claim 1, wherein the dose is 0.005 mg/kg/day or less.

4. The method according to claim 1, wherein the dose is 0.003 mg/kg/day or less.

5. The method according to claim 1, wherein the administration is performed during less than one month.

6. The method according to claim 1, wherein the growth hormone is human growth hormone.

7. The method according to claim 6, wherein the dose is less than 0.008 mg/kg/d.

8. The method according to claim 6, wherein the dose is 0.005 mg/kg/d or less.

9. The method according to claim 6, wherein the dose is 0.003 mg/kg/d or less.

10. The method according to claim 6, wherein growth hormone is administered during a period of less than one month.

11. The method according to claim 6, wherein the dose is 0.007 mg/kg/d or less.

12. The method according to claim 1, wherein the dose is 0.007 mg/kg/d or less.

* * * * *